United States Patent
Antonino

(10) Patent No.: US 9,950,089 B2
(45) Date of Patent: Apr. 24, 2018

(54) AROMATHERAPY APPARATUS AND HOUSING

(71) Applicant: Jason Carl Antonino, Phoenix, AZ (US)

(72) Inventor: Jason Carl Antonino, Phoenix, AZ (US)

(*) Notice: Subject to any disclaimer, the term of this patent is extended or adjusted under 35 U.S.C. 154(b) by 224 days.

(21) Appl. No.: 15/059,294

(22) Filed: Mar. 2, 2016

(65) Prior Publication Data

US 2016/0287738 A1    Oct. 6, 2016

Related U.S. Application Data

(60) Provisional application No. 62/140,404, filed on Mar. 30, 2015.

(51) Int. Cl.
*A61H 1/00* (2006.01)
*A61L 9/12* (2006.01)
(Continued)

(52) U.S. Cl.
CPC .............. *A61L 9/12* (2013.01); *A47G 9/1045* (2013.01); *A61H 15/0078* (2013.01); *A61L 9/04* (2013.01); *A61L 9/14* (2013.01); *A61M 21/02* (2013.01); *H04S 7/307* (2013.01); *A47G 9/1009* (2013.01); *A61H 23/02* (2013.01); *A61H 2201/0134* (2013.01); *A61H 2201/02* (2013.01); *A61H 2201/0207* (2013.01); *A61H 2201/102* (2013.01); *A61H 2201/1604* (2013.01); *A61H 2201/5007* (2013.01); *A61H 2201/5048* (2013.01); *A61L 2209/12* (2013.01); *A61M 2021/0016* (2013.01); *A61M 2021/0022* (2013.01); *A61M 2021/0027* (2013.01); *A61M 2021/0066* (2013.01); *A61M 2205/3569* (2013.01); *A61M 2205/3592* (2013.01); *A61M 2205/505* (2013.01); *H04S 1/007* (2013.01)

(58) Field of Classification Search
CPC ....... A61M 21/02; A47G 9/10; A47G 9/1009; A47G 9/1045; A61L 9/12
See application file for complete search history.

(56) References Cited

U.S. PATENT DOCUMENTS

| 5,266,070 | A |   | 11/1993 | Hagiwara |
| 6,023,801 | A | * | 2/2000  | Lamm ................ A47G 9/1009 5/636 |

(Continued)

FOREIGN PATENT DOCUMENTS

WO    WO2009079694 A1    7/2009

*Primary Examiner* — Kristen Matter

(57) ABSTRACT

The present invention is an apparatus for employing aromatherapy and binaural sounds for inducing a state of relaxation in a user who may be anxious, upset, or experiencing sleeping difficulties. The apparatus comprises a shape memory foam pillow, a pair of stereo speakers, an aromatherapy diffuser, a pillowcase comprised of heat-transfer fabric, an optional vibrating device, a canopy and a housing to support these elements. The user connects a smartphone or digital audio device to the speakers, activates the aromatherapy diffuser and the vibrating device, and lays his or her head down on the pillow beneath the canopy. Ideally, the smartphone or music device should have a meditation or binaural sound application, which would be tuned to a specific beat frequency, such as 10 Hertz. The combined action of essential oil vapors and binaural sounds should enable the user to relax or sleep more soundly.

9 Claims, 5 Drawing Sheets

(51) Int. Cl.
*A61L 9/04* (2006.01)
*A61H 15/00* (2006.01)
*A61L 9/14* (2006.01)
*A61M 21/02* (2006.01)
*H04S 7/00* (2006.01)
*A47G 9/10* (2006.01)
*H04S 1/00* (2006.01)
*A61M 21/00* (2006.01)
*A61H 23/02* (2006.01)

(56) References Cited

U.S. PATENT DOCUMENTS

| | | |
|---|---|---|
| 7,578,783 B2 | 8/2009 | Klein |
| 8,070,669 B2 | 12/2011 | Brunelle |
| 8,566,986 B1 * | 10/2013 | Chu ................ A47G 9/1045 |
| | | 5/636 |
| 2007/0068515 A1 | 3/2007 | Churchill |
| 2012/0209058 A1 | 8/2012 | Soroush |
| 2013/0254999 A1 * | 10/2013 | Foch ................... A47G 9/10 |
| | | 5/639 |
| 2013/0270880 A1 | 10/2013 | Lee |
| 2014/0008036 A1 | 1/2014 | Segal |
| 2014/0053338 A1 * | 2/2014 | White ............... A47G 9/1045 |
| | | 5/641 |
| 2015/0016613 A1 | 1/2015 | Atwater |
| 2015/0025606 A1 | 1/2015 | Davis |
| 2015/0047646 A1 | 2/2015 | Marinkovic |
| 2015/0334482 A1 * | 11/2015 | Rawls-Meehan ........ H04R 5/02 |
| | | 381/333 |
| 2016/0055842 A1 * | 2/2016 | DeFranks ............. A47G 9/10 |
| | | 381/66 |

* cited by examiner

AROMATHERAPY APPARATUS AND HOUSING

CROSS REFERENCE TO RELATED APPLICATION

This non-provisional application for patent hereby claims priority under 35 U.S.C. § 119(e) to U.S. Provisional Application No. 62/140,404, filed on Mar. 30, 2015, the contents of which are incorporated herein by reference in their entirety.

BACKGROUND OF THE INVENTION

The present invention relates to aromatherapy, in particular, the diffusion of essential oils in living quarters. Essential oils have been used in aromatherapy applications at various times throughout history Essential oils of lavender, bergamot, clary sage, vetiver, and ylang ylang, to name a few, have been used for treatment of nervous tension and inducing relaxation.

The present invention also relates to the use of binaural sounds for the purpose of altering emotional states. Binaural sounds are comprised of two separate sound channels vibrating at different frequencies, presented to a user simultaneously through headphones or speakers. The frequency difference between the two sounds is termed the binaural beat frequency, which is what the user experiences, and causes a shift in his or her brain wave frequency.

The present invention further relates to specially-shaped memory foam pillows for optimal support of a person's head, so as to ease muscle strain, thereby promoting quality sleep.

The invention still further relates to heat-transfer fabric so as to keep a user's skin temperature constant, thereby making the user more comfortable.

The invention further relates to a vibrating element for the purpose of providing a gentle massaging action to the user's head.

Finally, the invention relates to a housing for supporting the above elements and an overhead canopy for providing protection from sunlight and a degree of privacy.

Many types of aromatherapy diffusers are known in the art. They are typically comprised of a plastic reservoir to hold a mixture of water and one or more essential oils, an ultrasonic vibrating component, and a cover with an orifice through which essential oil vapors are directed. Some diffusers also display changing colors for ambience. The "Now® Ultrasonic Oil Diffuser" is such an example.

Binaural sound devices and applications are known in the art. They are typically marketed as software installed on desktop and portable computers for the purpose of playing binaural soundtracks through stereo headphones or speakers. A state of relaxation or sleepiness can be induced by entraining a user's brainwaves from the wide-awake beta range downward into alpha, and then into theta. US 2015/0016613 A1 "Spatial angle modulation binaural sound system," to Fredrick Atwater, et al., discloses a method of inducing a state of conscious in a listener by providing first and second sound signals to a user's left and right ear, respectively.

Contoured shape memory foam pillows are also well known in the art. US 2015/0047646 A1 "Therapeutic pillow," to John Marinkovic, discloses a contoured pillow for neck support and correction. The "Sleep Innovations Contour Memory Foam Pillow," sold through Amazon.com, relieves neck, shoulder and back pain by allowing neck and shoulder muscles to fully relax, and the pillow promotes proper spinal alignment. A number of other entities market and sell similar pillows.

Systems and methods for cooling a pillow exist in the art. For example, US 2015/0025606 A1 "Pillow integrated cooling system," to James Elliott Davis, discloses a system that can constantly transport a fluid throughout a pillow in order to keep the fluid at a desired temperature. The system uses fluid from a tank or reservoir that can be heated or cooled by a radiator prior to being filtered and distributed through tubes placed in the interior of the pillow.

US 2014/0053338 A1 "Aromatic air effusion apparatus for a pillow," to Chester Lewis White, discloses an aromatic air effusion apparatus for a pillow for both leisure relaxation and sleep retirement at night. The apparatus provides a user with a variety of aromatic scents that can be mechanically diffused throughout the interior of the pillow.

At this time, there are no aromatherapy devices that provide the benefits of essential oil diffusion with binaural sounds, vibration, heat-transfer fabric, a canopy, and a sturdy, portable housing. This invention combines all of these desirable features.

SUMMARY OF THE INVENTION

This is an aromatherapy apparatus that combines the features of essential oils diffused into the air, binaural sounds provided by a pair of stereo speakers, a contour shape memory foam pillow with a heat-transfer fabric pillowcase, a vibrating element disposed inside the pillowcase, a housing to support these features, and a canopy disposed over the apparatus to provide protection from sunlight (if used outdoors) and a measure of privacy.

These and other aspects and advantages of the invention will become apparent to those with ordinary skill in the art through the following description and drawings, which illustrate the features of the present invention.

DETAILED DESCRIPTION OF THE INVENTION

This is an aromatherapy apparatus that combines the features of essential oils diffused into the air, binaural sounds provided by a pair of stereo speakers, a contour shape memory foam pillow with a heat-transfer fabric pillowcase to keep the user cool, a vibrating element disposed inside the pillowcase, a housing to support these features, and a canopy disposed over the apparatus to provide protection from sunlight (if used outdoors) and a measure of privacy.

Figure 1:
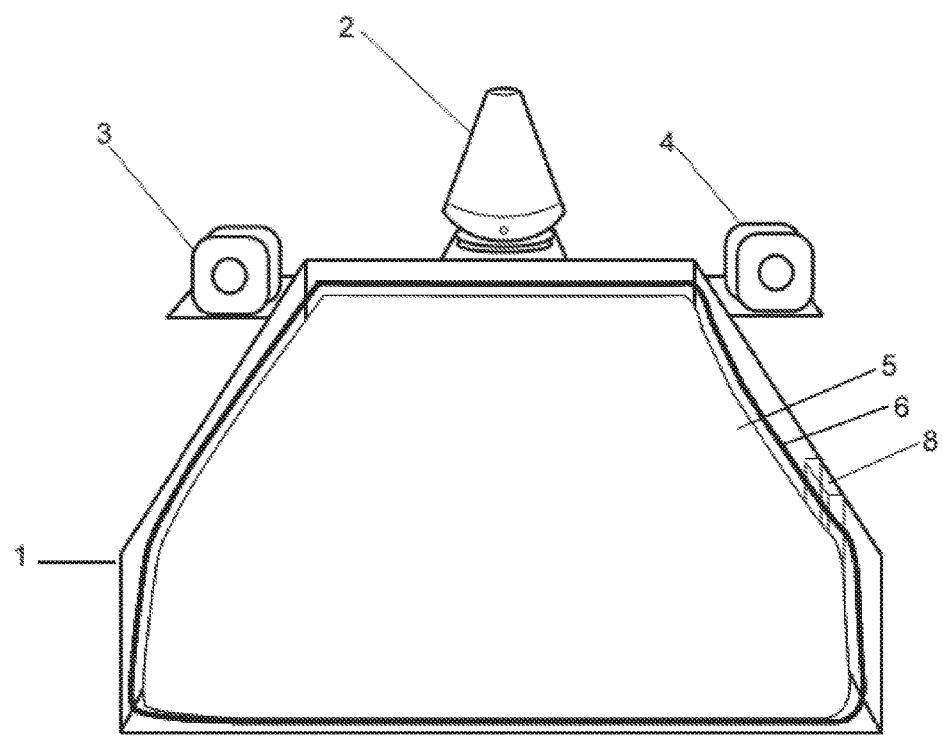
FIG. 1 is a perspective view of the fully assembled apparatus, without the canopy.

FIG. 1 shows a perspective view of the preferred embodiment of the invention. The apparatus includes a housing 1, aromatherapy diffuser 2, left speaker 3, right speaker 4, contour shape memory foam pillow 5 disposed inside pillowcase 6, input cable 7 for insertion into a smartphone or other digital device (not shown), vibrating element control 8, and a canopy 9, which is not shown.

The housing 1, in this embodiment, was fabricated from oriented strand board (OSB), which is an engineered wood particle board formed by adding adhesives and then compressing layers of wood strands (flakes) in specific orientations. The OSB in this invention was purchased from The Home Depot, although one of ordinary skill in the art would understand that this material may be obtained from a plurality of sources. Further, one of ordinary skill would also appreciate that other materials may be used to fabricate the housing, such as polyethylene, or other plastics.

The housing 1 consists of seven pieces: a bottom, left wall, right wall, rear wall, left speaker support, right speaker support, and diffuser support. These pieces were joined using Gorilla Glue, although one of ordinary skill would understand that mechanical fasteners could also be used. The joints were reinforced with Gorilla Glue Tape. The left speaker support was joined to the left wall, the right speaker support to the right wall, and the diffuser support to the rear wall. The vibrating element control 8 is secured to the right wall with the clip on the rear of the vibrating element control housing.

One of ordinary skill would understand that the housing could be fabricated from a single injection-molded piece of plastic. This description is not intended to limit the types of materials that could be used to form the housing, and any number of pieces may be used to construct the housing, as long as proper support is provided to the speakers, diffuser, pillow, vibrating element and canopy.

Figure 2:
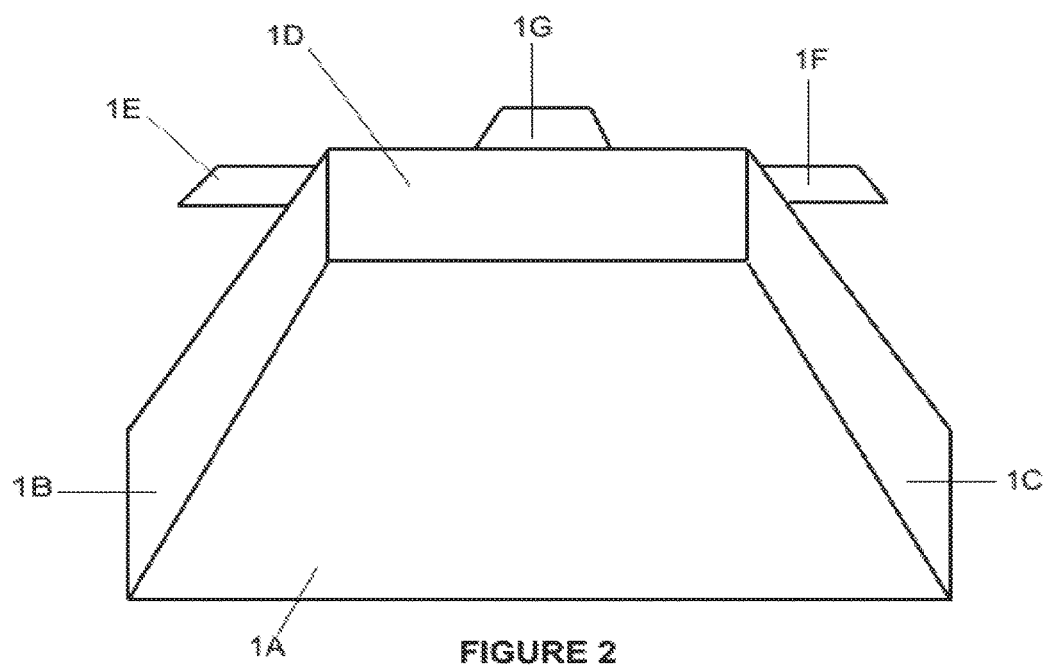
FIG. 2 is a view of the housing.

FIG. 2 is a view of the housing 1. The bottom is represented by 1A, the left wall 1B, right wall 1C, rear wall 1D, left speaker support 1E, right speaker support 1F, and diffuser support 1G.

Figure 3:
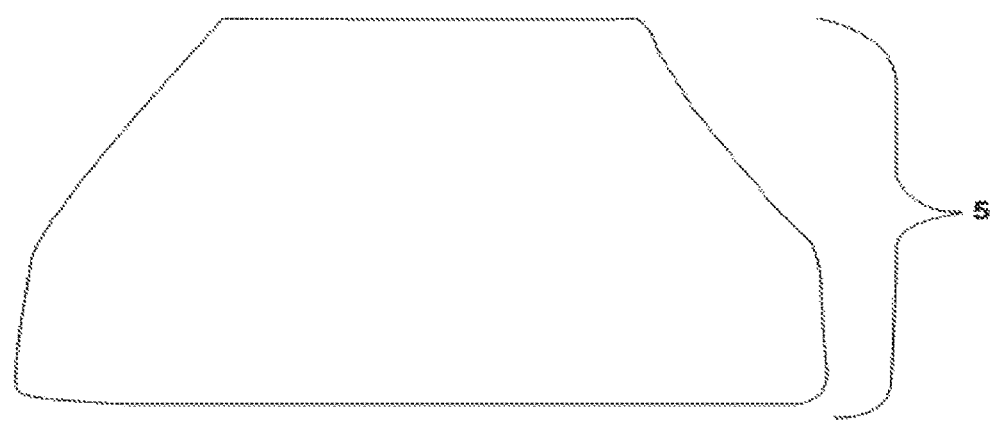
FIG. 3 is a view of the contour shape memory foam pillow.

FIG. 3 is a view of the contour shape memory foam pillow 5, in this example, the "Sleep Innovations Contour Memory Foam Pillow," purchased from Amazon.com.

Figure 4:
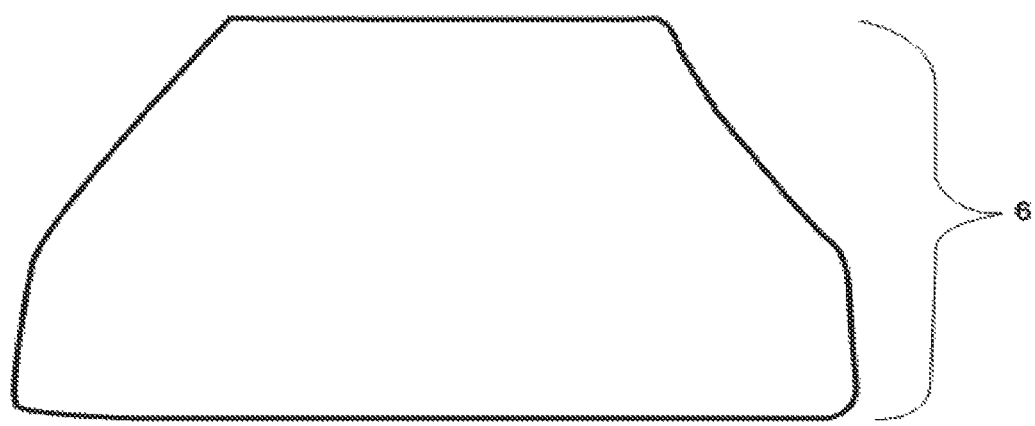
FIG. 4 is a view of the heat-transfer fabric pillowcase.

FIG. 4 is a view of the heat-transfer fabric pillowcase 6, in this example, the "Outlast White Standard Pillow Cover" manufactured by Outlast, and purchased from Slumbercloud.com.

Figure 5:
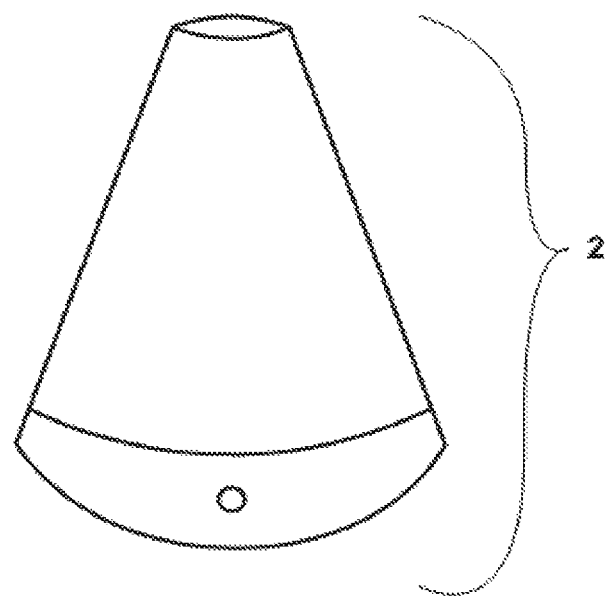
FIG. 5 is a view of the aromatherapy diffuser.

FIG. 5 is a view of the aromatherapy diffuser 2, in this example, "Now® Ultrasonic Oil Diffuser" purchased from Hi-Health.

Figure 6:
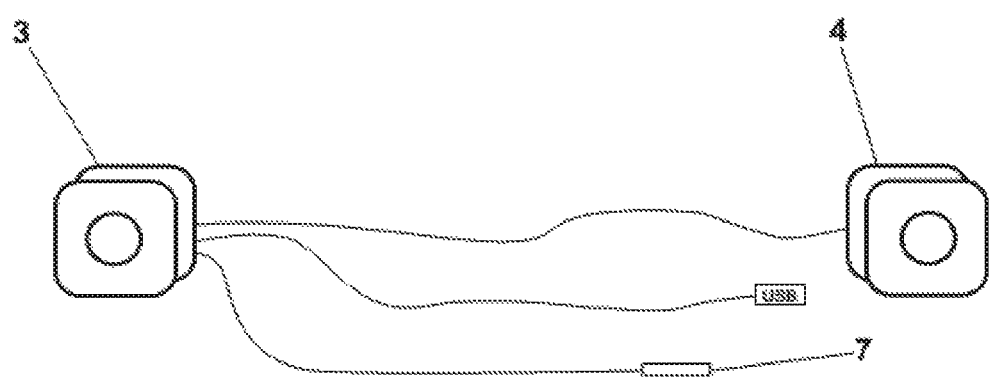
FIG. 6 is a view of the pair of stereo speakers and input jack.

FIG. 6 is a view of the set of stereo speakers 3, 4, and input cable 7. In this example, the "ARCTIC S111 USB-Powered Portable Stereo Speakers" were purchased from Amazon.com.

Figure 7:
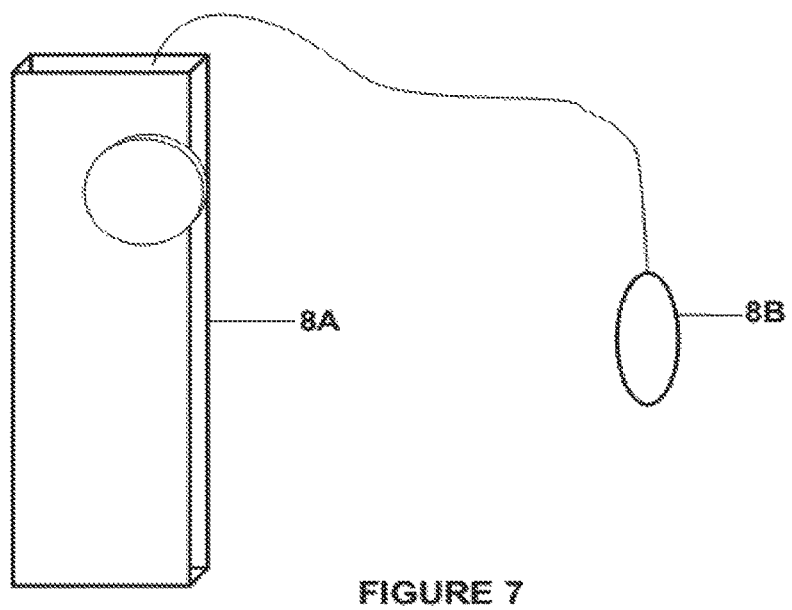
FIG. 7 is a view of the vibrating element.

FIG. 7 is a view of the vibrating element 8, in this example, manufactured and sold by Swedish Erotica. The vibrating element 8 consists of control 8A and vibrating egg 8B.

Figure 8:
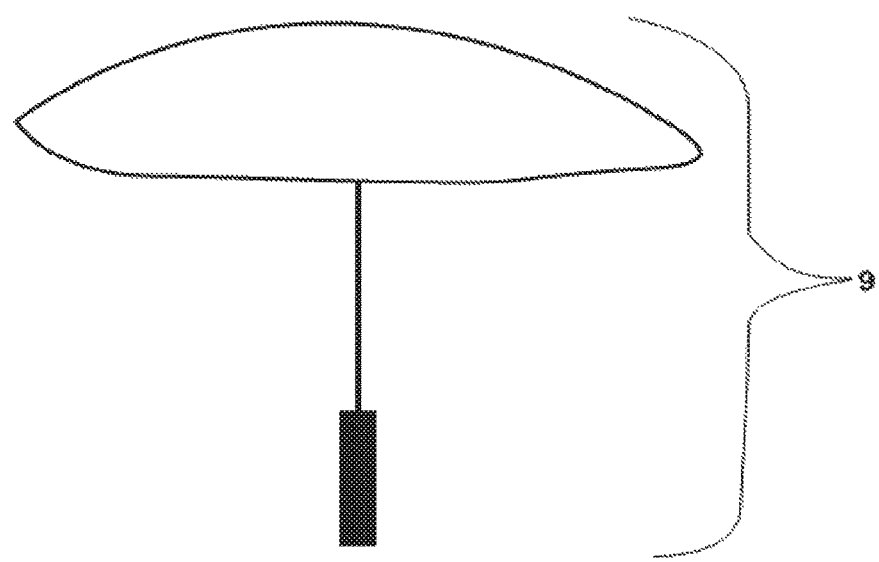
FIG. 8 is a view of the canopy.

FIG. 8 is a view of the canopy 9, in this example, a small umbrella, which can be obtained from most department stores.

The aromatherapy diffuser 2, and speakers 3, 4 must first be plugged into a 120 volt AC electrical outlet, prior to using the apparatus. The speakers 3 and 4 are placed on top of speaker supports 1E and 1F, respectively. In the preferred embodiment, a power strip is utilized to make the process easier, however, this is not required. A power strip is not a part of the invention.

In normal operation, a user would add a small quantity of water and one or more essential oils to the reservoir in the diffuser 2, which is placed on top of diffuser support 1G. Essential oils used for relaxation include lavender, vetiver, frankincense, ylang ylang, etc., alone or in combination. After the water and essential oil(s) have been added, the user presses the button to turn on the diffuser.

The user then plugs the speaker input jack 7 into a smartphone, such as an iPhone, or other digital audio device, equipped with binaural sound software, or a meditation application. The invention does not include a smartphone or digital audio device. The user then accesses the desired software or app, and selects an appropriate meditation soundtrack or binaural beat frequency, ideally in the alpha range of 7 to 10 Hertz for relaxation, or within the theta range of 4 to 7 Hertz for sleep induction.

The user then lays his or her head on the pillow a and pillowcase 6, and, if desired, activates the vibrating element 8 by switching the control 8A to the on position, and rotating the wheel to the desired vibrational intensity. The vibrating egg 8B is disposed beneath the pillowcase 6, on top of the pillow 5, so as to be directly beneath the user's head while he or she is lying down. The vibrating element control 8A can be clipped to the left wall 1B or right wall 1C of the housing 1 or simply held in the user's hand during use.

The canopy 9, if used, is secured to the rear wall 1D of the housing 1 while in use.

After a period of time has elapsed (at least 15 minutes), the user should begin to feel more relaxed, and may fall asleep. The aromatherapy diffuser in this example will continue to run until the reservoir is empty. Other diffusers have built-in timers that deactivate the diffuser after a particular duration, for example, 20 minutes. One of ordinary skill would understand that a variety of different diffusers may be used with this invention, and not limited to the specific model mentioned above.

It is not necessary for the diffuser 2, the binaural sounds, meditation sounds or music being played through speakers 3 and 4 and the vibrating element 8 to be in use simultaneously; one of ordinary skill would assume that these features can be used independently or in any combination, depending on the therapy desired.

It is understood that the embodiment presented in this description and drawings is meant to be exemplary. Embodiments of the present invention can comprise any combination of compatible features shown in the various figures, and these embodiments should not be limited to those expressly illustrated and discussed, and without departing from the scope and spirit of the invention as set forth in the following claims.

For the purposes of this invention, the masculine grammatical gender subsumes the feminine gender.

I claim:
1. An aromatherapy apparatus comprising:
   a housing comprising a bottom wall, a left wall, a right wall, and a rear wall;
   a contoured shape-memory foam pillow located on said bottom wall, said pillow disposed within a fabric pillowcase;
   a pair of speakers including an audio input cable, each speaker located on a respective speaker support piece attached to said housing;
   an aromatherapy diffuser located on a diffuser support piece attached to said housing;
   a vibrating element for imparting vibrations to said pillow; and
   a canopy secured to said housing.
2. The apparatus of claim 1, wherein said vibrating element comprises a vibrating egg disposed inside said pillowcase.

3. The apparatus of claim 1, wherein said vibrating element includes a control secured to either said left wall or said right wall.

4. The apparatus of claim 1, wherein said housing is fabricated from wood or plastic.

5. The apparatus of claim 1, wherein one of said speaker support pieces is attached to said left wall, and the other of the said speaker support pieces is attached to said right wall; and wherein said diffuser support piece is attached to said rear wall.

6. The apparatus of claim 1, wherein said canopy is secured to said rear wall.

7. The apparatus of claim 1, wherein said speakers are connected to a smartphone or portable music player via said audio input cable.

8. The apparatus of claim 1, wherein said aromatherapy diffuser contains a mixture of water and essential oils.

9. A method of using an aromatherapy apparatus, the method comprising:

adding water to an aromatherapy diffuser, said aromatherapy diffuser disposed on a support piece of a housing, said housing in the form of an open container;

adding one or more essential oils to the water in said aromatherapy diffuser, and activating said aromatherapy diffuser;

connecting a user-supplied smartphone or portable music player to a pair of portable stereo speakers, each of said speakers disposed on a respective support piece of said housing, and activating any one of a music application or binaural beats application preinstalled on said user's smartphone or music player;

deploying a canopy secured to said housing;

the user laying his head down on a pillow, said pillow disposed within said housing, and said pillow encased within a pillowcase; and activating a vibrating element for imparting vibrations to said pillow.

* * * * *